United States Patent
Ranayhossaini et al.

(10) Patent No.: US 9,770,481 B2
(45) Date of Patent: Sep. 26, 2017

(54) INHIBITORS OF NOX1

(71) Applicant: UNIVERSITY OF PITTSBURGH—OF THE COMMONWEALTH SYSTEM OF HIGHER EDUCATION, Pittsburgh, PA (US)

(72) Inventors: Daniel J. Ranayhossaini, Pittsburgh, PA (US); Patrick Joseph Pagano, Sewickley, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 14/879,843

(22) Filed: Oct. 9, 2015

(65) Prior Publication Data

US 2016/0089414 A1  Mar. 31, 2016

Related U.S. Application Data

(60) Division of application No. 14/276,564, filed on May 13, 2014, now Pat. No. 9,187,528, which is a continuation of application No. PCT/US2012/065322, filed on Nov. 15, 2012.

(60) Provisional application No. 61/560,075, filed on Nov. 15, 2011, provisional application No. 61/654,485, filed on Jun. 1, 2012.

(51) Int. Cl.
*A61K 38/08* (2006.01)
*C07K 7/06* (2006.01)
*A61P 35/00* (2006.01)
*A61K 38/00* (2006.01)
*C07K 16/28* (2006.01)

(52) U.S. Cl.
CPC ............ *A61K 38/08* (2013.01); *A61K 38/005* (2013.01); *C07K 7/06* (2013.01); *C07K 16/2803* (2013.01); *A61K 38/00* (2013.01)

(58) Field of Classification Search
CPC ...... A61K 38/08; A61K 38/00; A61K 38/005; C07K 16/2803; C07K 7/06
See application file for complete search history.

(56) References Cited

U.S. PATENT DOCUMENTS 5,595,756 A * 1/1997 Bally .................. A61K 9/1272
                                                        264/4.1
9,187,528 B2   11/2015 Ranayhossaini et al.

FOREIGN PATENT DOCUMENTS

JP  2005-168329     6/2005
WO  WO 99/09175 A1  2/1999

OTHER PUBLICATIONS

Altenhofer et al, Evolution of NADPH Oxidase Inhibitors: Selectivity and Mechanisms for Target Engagement, Antioxidants & Redox Signaling, 2015, 23, pp. 406-427.*
Panday et al, NADPH oxidases: an overview from structure to innate immunity-associated pathologies, Cellular & Molecular Immunology, 2015, 12, pp. 5-23.*
Brieger et al, Reactive oxygen species: from health to disease, Swiss Med Wkly., 2012, 142:w13659, pp. 1-14.*
Alfadda et al, Reactive Oxygen Species in Health and Disease, Journal of Biomedicine and Biotechnology, 2012, pp. 1-14.*
Sporn, B and Suh, N, Chemoprevention of cancer, Carcinogenesis, 2000, 21, pp. 525-530.*
Auerbach. R. et al, Angiogenesis assays: Problems and pitfalls, Cancer and Metastasis Reviews, 2000, 19, pp. 167-172.*
Gura, T. Systems for Identifying New Drugs Are Often Faulty, Science, 1997, 278, pp. 1041-1042.*
Jain R. K., Barriers to Drug Delivery in Solid Tumors, Scientific American, 1994, pp. 58-65.*
Cancer Drug Design and Discovery. Neidle, Stephen, ed., Elsevier/ACademic Press, 2008, p. 427-431.*
Cellular and Molecular Basis of Cancer, from http://www.merckmanuals.com/professional/print/hematology_and_oncology/overview_of . . . , pp. 1-5, accessed Nov. 7, 2012.*
U.S. Appl. No. 14/276,564 (U.S. Pat. No. 9,187,528), May 13, 2014 (Nov. 17, 2015).
U.S. Appl. No. 14/276,564, Oct. 9, 2015 Issue Fee Payment.
U.S. Appl. No. 14/276,564, Sep. 2, 2015 Notice of Allowance.
U.S. Appl. No. 14/276,564, Jun. 4, 2015 Response to Restriction Requirement.
U.S. Appl. No. 14/276,564, Feb. 4, 2015 Restriction Requirement Filed.
Al Gouleh et al., "Oxidase and peroxidases in cardiovascular and lung disease: New concepts in reactive oxygen species signaling", Free Radic. Biol. Med., 51(7):1271-1288 (2011).
Diatchuk et al., "Inhibition of NADPH oxidase activation by 4-(2-aminoethyl)-benzenesulfonyl fluoride and related compounds", The Journal of Biological Chemistry, 272(20):13292-13301 (1997).
Dikalova et al., "Nox 1 overexpression potentiates angiotensin II-induced hypertension and vascular smooth muscle hypertrophy in transgenic mice", Circulation, 112(17):2668-2676 (2005).
Gianni et al., "A novel and specific NADPH oxidase-1(Nox 1) small-molecule inhibitor blocks the formation of functional invadopodia in human colon cancer cells", ACS Chem. Biol., 5(10):981-983 (2010).

(Continued)

*Primary Examiner* — Julie Ha
*Assistant Examiner* — Li Ni Komatsu
(74) *Attorney, Agent, or Firm* — Baker Botts L.L.P.

(57) ABSTRACT

The present invention relates to inhibitors of Nox1-dependent reactive oxygen species production and their use in the treatment of disorders associated with reactive oxygen species, such as hypertension and cancer.

3 Claims, 15 Drawing Sheets

(56) References Cited

OTHER PUBLICATIONS

Han et al., "Regulation of the neutrophil respiratory burst oxidase. Identification of an activation domain in p67(phox)", J. Biol. Chem., 273(27):16663-16668 (1998).

Howard et al., "Cyclic strain induces an oxidative stress in endothelial cells", Am. J. Physiol. Cell Physiol., 212(2):C421-C427 (1997).

International Search Report and Written Opinion for PCT/US2012/065322, dated May 30, 2013.

Jaquet et al., "NADPH oxidase (NOX) isoforms are inhibited by celastrol with a dual mode of action", British Journal of Pharmacology, 164:507-520 (Aug. 2011).

Kim et al., "NADPH oxidase inhibitors: a patent review", Expert Opin ther Pat., 21(8):1147-1158 (2011).

Maehara et al., "A conserved region between the TPR and activation doamins of p67phox participates in activation of the phagocyte NADPH oxidase", J. Biol. Chem., 285(41):31435-31445 (2010).

Nisimoto et al., "The p67(phox) activation domain regulates electron flow from NADPH to flavin in flavocytochrome b(558)", J. Biol. Chem., 274(33):22999-30005 (1999).

Rey et al., "Novel competitive inhibitor of NAD(P)H oxidase assembly attenuates vascular $O(2)(-)$ and systolic blood pressure in mice", Circ. Res., 89(5):408-414 (2001).

Standley et al., "Cyclic stretch induces vascular smooth muscle cell alignment via NO signaling", Am. J. Physiol. Heart, 283(5):H1907-H1914 (2002).

Stielow et al, Novel Nox inhibitor of oxLDL-induced reactive oxygen species formation in human endothelial cells, Biochemical and Biophysical Research Communications, 2006, 344, pp. 200-205.

White et al., "Superoxide and peroxinitrite in atherosclerosis", PNAS, 91(3):1044-1048 (1994).

Yu et al., "Biosynthesis of the phagocyte NADPH oxidase cytochrome b558. Role of heme incorporation and heterodimer formation in maturation and stability of gp91phox and p22phox subunits", J. Biol. Chem., 272(43):27288-27294 (1997).

\* cited by examiner

P67phox: 190-VAQLAKKDYLGKATVVSVVD-209

NOXA1:  191-LKHLEPVDFLGKAKVVASAI-210
              * * *

B.

NOXA1 GenBank Accession No. NM_006647

MASLGDLVRAWHLGAQAVDRGDWARALHLFSGVPAPPARLCFNAGCVHLL
AGDPEAALRAFDQAVTKDTCMAVGFFQRGVANFQLARFQEALSDFWLALE
QLRGHAAIDYTQLGLRFKLQAWEVLHNVASAQCQLGLWTEAASSLREAMS
KWPEGSLNGLDSALDQVQRRGSLPPRQVPRGEVFRPHRWHLKHLEPVDFL
GKAKVVASAIPDDQGWGVRPQQPQGPGANHDARSLIMDSPRAGTHQGPLD
AETEVGADRCTSTAYQEQRPQVEQVGKQAPLSPGLPAMGGPGPGPCEDPA
GAGGAGAGGSEPLVTVTVQCAFTVALRARRGADLSSLRALLGQALPHQAQ
LGQLSYLAPGEDGHWVPIPEEESLQRAWQDAAACPRGLQLQCRGAGGRPV
LYQVVAQHSYSAQGPEDLGFRQGDTVDVLCEEPDVPLAVDQAWLEGHCDG
RIGIFPKCFVVPAGPRMSGAPGRLPRSQQGDQP

FIGURE 2

NOXA1:              191-LKHLEPVDFLGKAKVVASAI-210
                                    *
NoxA1ds:            [NH3]-EPVDALGKAKV-[CONH2]
NoxA1ds SCRMB2:     [NH3]-LVKGPDAEKVA-[CONH2]

FIGURE 3A-B
A.
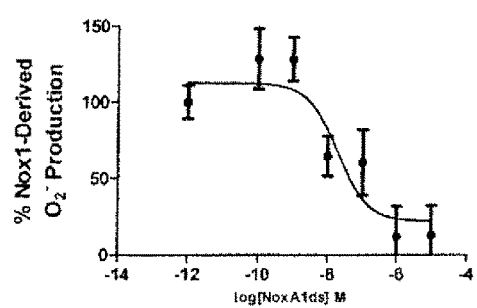
B.
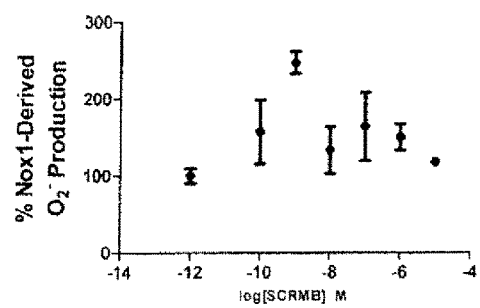

FIGURE 4A-D
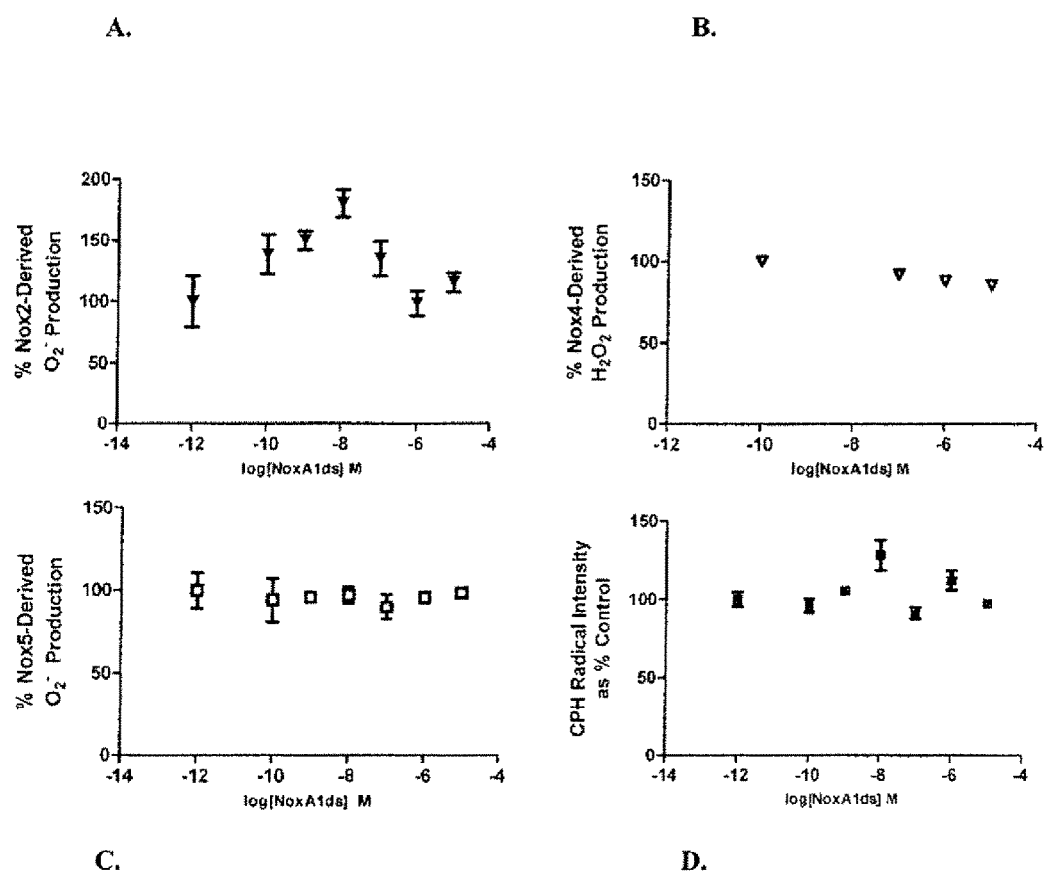

FIGURE 6A-B
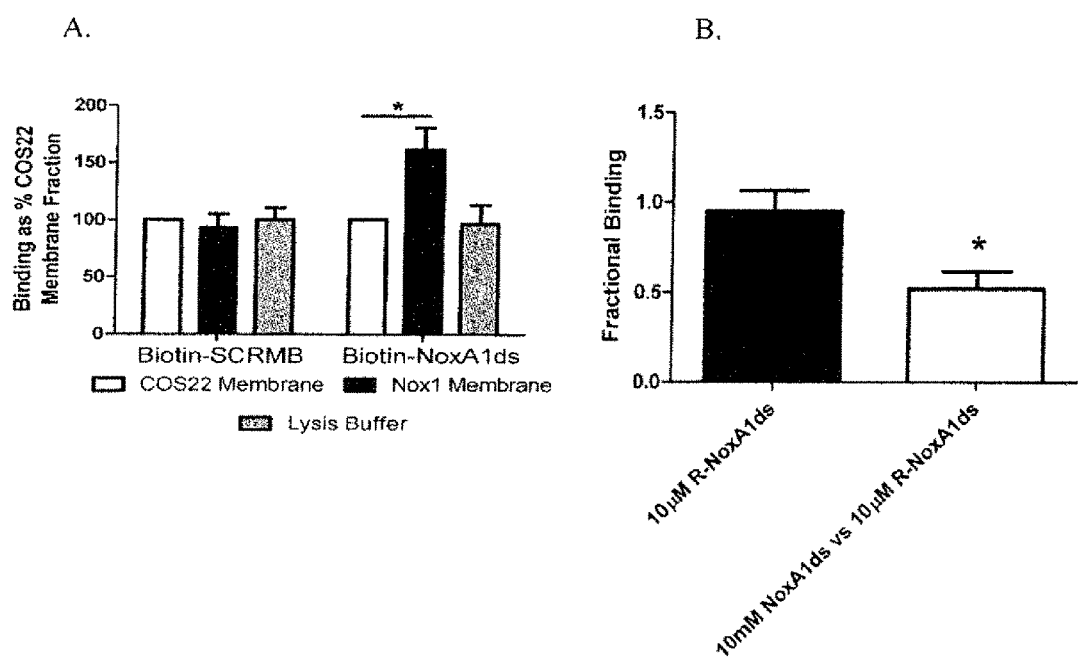

SEQUENCE LISTING

```
<160> NUMBER OF SEQ ID NOS: 17

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (5)..(5)
<223> OTHER INFORMATION: Any natural or non-natural amino acid other
      than Phe
<220> FEATURE:
<223> OTHER INFORMATION: C-term CONH2

<400> SEQUENCE: 1

Glu Pro Val Asp Xaa Leu Gly Lys Ala Lys Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (4)..(4)
<223> OTHER INFORMATION: Any natural or non-natural amino acid other
      than Phe
<220> FEATURE:
<223> OTHER INFORMATION: C-term CONH2

<400> SEQUENCE: 2

Pro Val Asp Xaa Leu Gly Lys Ala Lys Val
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: N-term NH3+
<220> FEATURE:
<221> NAME/KEY: MOD_RES
<222> LOCATION: (5)..(5)
<223> OTHER INFORMATION: Any natural or non-natural amino acid other
      than Phe
<220> FEATURE:
<223> OTHER INFORMATION: C-term CONH2

<400> SEQUENCE: 3

Glu Pro Val Asp Xaa Leu Gly Lys Ala Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (3)..(3)
<223> OTHER INFORMATION: Any natural or non-natural amino acid other
      than Phe
<220> FEATURE:
<223> OTHER INFORMATION: C-term CONH2

<400> SEQUENCE: 4

Val Asp Xaa Leu Gly Lys Ala Lys Val
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (2)..(2)
<223> OTHER INFORMATION: Any natural or non-natural amino acid other
      than Phe
<220> FEATURE:
<223> OTHER INFORMATION: C-term CONH2

<400> SEQUENCE: 5

Asp Xaa Leu Gly Lys Ala Lys Val
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (3)..(3)
<223> OTHER INFORMATION: Any natural or non-natural amino acid other
      than Phe
<220> FEATURE:
<223> OTHER INFORMATION: C-term CONH2

```
<400> SEQUENCE: 6

Val Asp Xaa Leu Gly Lys Ala
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<223> OTHER INFORMATION: C-term CONH2

<400> SEQUENCE: 7

Glu Pro Val Asp Ala Leu Gly Lys Ala Lys Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (5)..(5)
<223> OTHER INFORMATION: Any natural or non-natural amino acid other
      than Phe
<220> FEATURE:
<223> OTHER INFORMATION: C-term CONH2

<400> SEQUENCE: 8

Glu Pro Val Asp Xaa Leu Gly Lys Ala Lys Val
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (3)..(3)
<223> OTHER INFORMATION: Any natural or non-natural amino acid other
      than Val
<220> FEATURE:
<223> OTHER INFORMATION: C-term CONH2

<400> SEQUENCE: 9

Glu Pro Xaa Asp Phe Leu Gly Lys Ala Lys Val
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term NH3+
<220> FEATURE:
<221> NAME/KEY: MOD_RES
<222> LOCATION: (4)..(4)
<223> OTHER INFORMATION: Any natural or non-natural amino acid other
      than Asp
<220> FEATURE:
<223> OTHER INFORMATION: C-term CONH2

<400> SEQUENCE: 10

Glu Pro Val Xaa Phe Leu Gly Lys Ala Lys Val
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (3)..(5)
<223> OTHER INFORMATION: Any amino acid as long as this region does not
      encompass 'Val Phe Asp'
<220> FEATURE:
<223> OTHER INFORMATION: C-term CONH2

<400> SEQUENCE: 11

Glu Pro Xaa Xaa Xaa Leu Gly Lys Ala Lys Val
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (5)..(5)
<223> OTHER INFORMATION: Ala, Val, Leu, Ile, Met, Tyr, Trp, Ser, Thr,
      Asn, Gln, Asp, Glu, Cys, Gly, Pro, Arg, His or Lys
<220> FEATURE:
<223> OTHER INFORMATION: C-term CONH2

<400> SEQUENCE: 12

Glu Pro Val Asp Xaa Leu Gly Lys Ala Lys Val
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<221> NAME/KEY: MOD_RES
<222> LOCATION: (5)..(5)
<223> OTHER INFORMATION: Ala, Val or Leu
<220> FEATURE:
<223> OTHER INFORMATION: C-term CONH2

<400> SEQUENCE: 13
```

Glu Pro Val Asp Xaa Leu Gly Lys Ala Lys Val
1               5                   10

<210> SEQ ID NO 14
<211> LENGTH: 20
<212> TYPE: PRT
<213> ORGANISM: Unknown
<220> FEATURE:
<223> OTHER INFORMATION: Description of Unknown: p67phox peptide

<400> SEQUENCE: 14

Val Ala Gln Leu Ala Lys Lys Asp Tyr Leu Gly Lys Ala Thr Val Val
1               5                   10                  15

Ser Val Val Asp
            20

<210> SEQ ID NO 15
<211> LENGTH: 20
<212> TYPE: PRT
<213> ORGANISM: Homo sapiens

<400> SEQUENCE: 15

Leu Lys His Leu Glu Pro Val Asp Phe Leu Gly Lys Ala Lys Val Val
1               5                   10                  15

Ala Ser Ala Ile
            20

<210> SEQ ID NO 16
<211> LENGTH: 483
<212> TYPE: PRT
<213> ORGANISM: Homo sapiens

<400> SEQUENCE: 16

Met Ala Ser Leu Gly Asp Leu Val Arg Ala Trp His Leu Gly Ala Gln
1               5                   10                  15

Ala Val Asp Arg Gly Asp Trp Ala Arg Ala Leu His Leu Phe Ser Gly
                20                  25                  30

Val Pro Ala Pro Pro Ala Arg Leu Cys Phe Asn Ala Gly Cys Val His
            35                  40                  45

Leu Leu Ala Gly Asp Pro Glu Ala Ala Leu Arg Ala Phe Asp Gln Ala
    50                  55                  60

Val Thr Lys Asp Thr Cys Met Ala Val Gly Phe Phe Gln Arg Gly Val
65                  70                  75                  80

Ala Asn Phe Gln Leu Ala Arg Phe Gln Glu Ala Leu Ser Asp Phe Trp
                85                  90                  95

Leu Ala Leu Glu Gln Leu Arg Gly His Ala Ala Ile Asp Tyr Thr Gln
            100                 105                 110

Leu Gly Leu Arg Phe Lys Leu Gln Ala Trp Glu Val Leu His Asn Val
        115                 120                 125

Ala Ser Ala Gln Cys Gln Leu Gly Leu Trp Thr Glu Ala Ala Ser Ser
    130                 135                 140

Leu Arg Glu Ala Met Ser Lys Trp Pro Glu Gly Ser Leu Asn Gly Leu
145                 150                 155                 160

Asp Ser Ala Leu Asp Gln Val Gln Arg Gly Ser Leu Pro Pro Arg
                165                 170                 175

Gln Val Pro Arg Gly Glu Val Phe Arg Pro His Arg Trp His Leu Lys
            180                 185                 190

His Leu Glu Pro Val Asp Phe Leu Gly Lys Ala Lys Val Val Ala Ser
        195                 200                 205

```
Ala Ile Pro Asp Asp Gln Gly Trp Gly Val Arg Pro Gln Gln Pro Gln
        210                 215                 220

Gly Pro Gly Ala Asn His Asp Ala Arg Ser Leu Ile Met Asp Ser Pro
225                 230                 235                 240

Arg Ala Gly Thr His Gln Gly Pro Leu Asp Ala Glu Thr Glu Val Gly
                245                 250                 255

Ala Asp Arg Cys Thr Ser Thr Ala Tyr Gln Glu Gln Arg Pro Gln Val
            260                 265                 270

Glu Gln Val Gly Lys Gln Ala Pro Leu Ser Pro Gly Leu Pro Ala Met
        275                 280                 285

Gly Gly Pro Gly Pro Gly Pro Cys Glu Asp Pro Ala Gly Ala Gly Gly
290                 295                 300

Ala Gly Ala Gly Gly Ser Glu Pro Leu Val Thr Val Thr Val Gln Cys
305                 310                 315                 320

Ala Phe Thr Val Ala Leu Arg Ala Arg Arg Gly Ala Asp Leu Ser Ser
                325                 330                 335

Leu Arg Ala Leu Leu Gly Gln Ala Leu Pro His Gln Ala Gln Leu Gly
            340                 345                 350

Gln Leu Ser Tyr Leu Ala Pro Gly Glu Asp Gly His Trp Val Pro Ile
        355                 360                 365

Pro Glu Glu Glu Ser Leu Gln Arg Ala Trp Gln Asp Ala Ala Ala Cys
        370                 375                 380

Pro Arg Gly Leu Gln Leu Gln Cys Arg Gly Ala Gly Gly Arg Pro Val
385                 390                 395                 400

Leu Tyr Gln Val Val Ala Gln His Ser Tyr Ser Ala Gln Gly Pro Glu
                405                 410                 415

Asp Leu Gly Phe Arg Gln Gly Asp Thr Val Asp Val Leu Cys Glu Glu
            420                 425                 430

Pro Asp Val Pro Leu Ala Val Asp Gln Ala Trp Leu Glu Gly His Cys
        435                 440                 445

Asp Gly Arg Ile Gly Ile Phe Pro Lys Cys Phe Val Val Pro Ala Gly
        450                 455                 460

Pro Arg Met Ser Gly Ala Pro Gly Arg Leu Pro Arg Ser Gln Gln Gly
465                 470                 475                 480

Asp Gln Pro

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH3+
<220> FEATURE:
<223> OTHER INFORMATION: C-term CONH2

<400> SEQUENCE: 17

Leu Val Lys Gly Pro Asp Ala Glu Lys Val Ala
1               5                   10
```

INHIBITORS OF NOX1

PRIORITY CLAIM

This application is a divisional of U.S. patent application Ser. No. 14/276,564 filed May 13, 2014, now U.S. Pat. No. 9,187,528 B2, issued on Nov. 17, 2015, which is a continuation of International Application No. PCT/US12/065322 filed Nov. 15, 2012, which claims priority to U.S. Provisional Application No. 61/560,075 filed Nov. 15, 2011 and to U.S. Provisional Application No. 61/654,485 filed Jun. 1, 2012, the contents of each of which are incorporated by reference in their entireties herein, and priority to each of which is claimed.

GRANT INFORMATION

This invention was made with government support under grant number NIH RO1 HL079207 awarded by the National Institutes of Health. The government has certain rights in the invention.

SEQUENCE LISTING

The specification further incorporates by reference the Sequence Listing submitted herewith via EFS on Oct. 9, 2015. Pursuant to 37 C.F.R. §1.52(e)(5), the Sequence Listing text file, identified as 0723960560DIVSEQLIST.txt, is 10,549 bytes and was created on Oct. 9, 2015. The Sequence Listing, electronically filed herewith, does not extend beyond the scope of the specification and thus does not contain new matter.

INTRODUCTION

The present invention relates to inhibitors of NADPH oxidase-1 (Nox1)-dependent reactive oxygen species (including superoxide) production and their use in the treatment of disorders associated with reactive oxygen species, such as hypertension and cancer and other Nox1-related conditions.

BACKGROUND OF THE INVENTION

NADPH oxidases (Nox) are proteins present in the membrane of a variety of mammalian cell types whose function is to produce reactive oxygen species (ROS) such as superoxide anion ($O_2^-$) and hydrogen peroxide ($H_2O_2$). Maintaining healthy $O_2^-$ levels is important in maintaining vascular tone. However, excessive $O_2^-$ production may lead to hypertension through scavenging of the vasodilatory agent nitric oxide (NO) [1]. In addition, Nox-dependent ROS production is critical in a number of cellular signaling pathways and is involved in multiple cardiovascular diseases and colon cancer. [See 6, 7.]

With this wide gamut of functions for ROS, tight regulation of Nox by the cell is required. This is accomplished in part by generation of a number of different isoforms of Nox that are differentially regulated and produced in varying cell types. Among these isoforms, Nox1 and Nox2 bear significant homology. Each of these isoforms associates with the membrane protein p22phox and cytosolic organizing and activating subunits. Nox1 was originally discovered in colon carcinoma cells and has more recently been found to cause deleterious vascular constriction and contribute to angiogenic processes [2]. Nox2 is the prototypical enzyme of the family and is responsible for the respiratory burst found in phagocytes [2].

Both Nox1 and Nox2 produce $O_2^-$ exclusively while Nox4 is thought to primarily produce $H_2O_2$ [2]. Nox1 and Nox2 derived $O_2^-$ directly inactivates NO. Cells use cytosolic cofactors to regulate Nox-derived ROS production. Nox4 appears not to require classical cytosolic factors as do Nox1 and 2 but recently Poldip2 has been described as modulatory for Nox4. Nox1 activation is regulated primarily by the cytosolic proteins NOXA1, NOXO1, and the GTPase Rac1 while Nox2 activation is primarily regulated by the cytosolic proteins p67phox, p47phox, p40phox, and the GTPase Rac2 [2].

NOXA1 shares 38.3% homology with p67phox and a specific domain of p67phox from amino acids 190-200 is particularly well conserved across the animal kingdom and shares high homology with NOXA1[3-5] (FIG. 1A-B). This domain has been termed the activation domain of p67phox and within it are a number of amino acids critical to the activation of Nox2. A portion of NOXA1 stretching from amino acids 191-211 is highly homologous to the activation domain of p67phox. Within these amino acids, 199-201 are of particular importance to enzyme activation (FIG. 1A). If one of these amino acids in NOXA1 is mutated to an alanine, the protein's function is reduced and in some cases totally lost [5].

SUMMARY OF THE INVENTION

The present invention relates to inhibitors of Nox1-dependent ROS production. It is based, at least in part, on the discovery of one such inhibitor, a peptide termed NoxA1ds, the amino acid sequence of which is [$NH_3^+$]-EPVDALG-KAKV-[CONH2](SEQ ID NO:7). NoxA1ds was shown to selectively inhibit superoxide production by Nox1 while having little or no significant inhibitory effect on superoxide production by Nox2 and Nox5 or on hydrogen peroxide production by Nox4. Accordingly, NoxA1ds and related peptides may be used to treat Nox1-related disorders, such as hypertension and colon carcinoma. The Nox1 selectivity of these inhibitors indicates that they would be less likely to have side effects related to inhibition of Nox2 or Nox4.

BRIEF DESCRIPTION OF THE FIGURES

FIG. 1A-B. (A) Sequence alignment of p67phox (SEQ ID NO:14) and NOXA1 (SEQ ID NO:15). Amino acids in bold share the highest homology between the Amino acids with a * indicate amino acids 199-201 where if one amino acid is mutated, the enzyme will be nonfunctional. (B) Human amino acid sequence of NOXA1 (GenBank Accession No. NM_006647) (SEQID NO:16).

FIG. 2. Sequence of NOXA1 (SEQ ID NO:15) used to derive NoxA1ds (SEQ ID NO:7). A point mutation at amino acid 199 was generated in the NoxA1ds peptide, indicated by the *. The inactive, scrambled version of NoxA1ds (NoxA1ds SCRMB2) (SEQ ID NO:17) is also shown.

FIG. 3A-B: NoxA1ds inhibits Nox1-derived $O_2^-$ production. COS22 cells were transfected with the Nox1 gene components and then treated with increasing concentrations of either (A) NoxA1ds or (B) scrambled control peptide (SCRMB), and production of $O_2^-$ was measured. Percent $O_2^-$ relative to untreated cells are shown. All values are expressed as n=9-12, 3-4 separate experiments.

FIG. 4A-D: NoxA1ds does not inhibit related enzymes Nox2, Nox 4, or Nox5. (A) COS22 cells were transfected with Nox2 oxidase, stimulated with LiDS, and treated with increasing concentrations of NoxA1ds. Percent $O_2^-$ relative to untreated cells are shown. (B) COS22 cells were transfected with Nox4 oxidase and treated with increasing concentrations of NoxA1ds. Percent $H_2O_2$ relative to untreated cells are shown. (C) HEK293 cells were transfected with Nox5 oxidase, stimulated with $Ca^{2+}$ and treated with increasing concentrations of NoxA1ds. Percent $O_2^-$ relative to untreated cells are shown. (D) Pure xanthine oxidase was stimulated with hypoxanthine and treated with increasing concentrations of NoxA1ds. In all panels, no inhibition of the signal was observed. n=9-12, three to four separate experiments.

FIG. 6A-B. (A) Results of ELISA-type assay where SCRMB or NoxA1ds were bound to solid phase and tested for ability to bind to membrane-bound Nox1 (COS membrane lacking Nox1 was used as a control). n=10-12, three separate experiments, *$p<0.05$, two-way ANOVA with Bonferroni post test. (B) Results of spectroscopy studies showing that unlabeled NoxA1ds could compete with rhodamine-labeled NoxA1ds for Nox1 binding. n=3, *$p<0.05$, one-way ANOVA with Bonferroni post test.

DETAILED DESCRIPTION OF THE INVENTION

Figure 5:
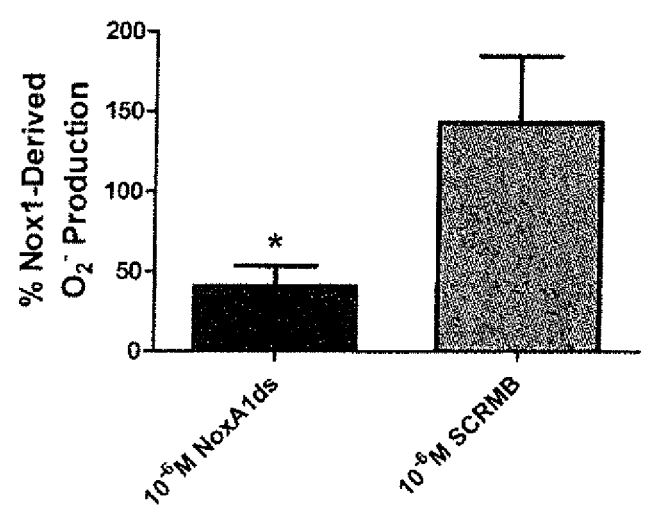
FIG. 5. Production of superoxide by HEK-Nox1 cells, measured via reduction of cytochrome c, after treatment with NoxA1ds or scrambled peptide (SCRMB; negative control).

The present invention relates to inhibitors of Nox1-dependent ROS production, and of superoxide ($O_2^-$) production in particular.

Nox1, Nox2 or Nox4 as referred to herein may be human or non-human enzymes. Where the relative activity of an inhibitor against Nox1 versus other NADPH oxidases such as Nox2 and Nox4 is described herein, the enzymes referred to should be assumed to derive from the same species unless specified otherwise.

In particular non-limiting embodiments of the invention the inhibitor of Nox1 is a selective inhibitor of Nox1, meaning that it has substantially less or essentially no inhibitory activity toward the ROS-generating activity of one or more other NADPH oxidases such as but not limited to Nox2, Nox3, Nox4, Nox5, Nox6 and/or Nox7 and/or xanthine oxidase ("XO"). In specific non-limiting embodiments the $IC_{50}$ of a Nox1 inhibitor of the invention is at least 10-fold or at least 50-fold or at least 100-fold or at least 1000-fold less than the $IC_{50}$ of said inhibitor for one or more other NADPH oxidases such as but not limited to Nox2, Nox3, Nox4, Nox5, Nox6 and/or Nox7.

In particular non-limiting embodiments of the invention the inhibitor of Nox1 comprises the amino acid sequence [$NH_3^+$]-EPVDX$_1$LGKAKV-[CONH$_2$] (SEQ ID NO:1) where $X_1$ is a natural or non-natural amino acid other than phenylalanine (F). In certain non-limiting embodiments $X_1$ is selected from the group consisting of alanine, valine, leucine, isoleucine, methionine, tyrosine, tryptophan, serine, threonine, asparagine, glutamine, aspartic acid, glutamic acid, cysteine, glycine, proline, arginine, histidine, and lysine. In certain non-limiting embodiments $X_1$ is selected from the group consisting of alanine, valine, leucine, isoleucine, methionine, tyrosine, and tryptophan. In certain non-limiting embodiments $X_1$ is selected from the group consisting of alanine, valine, leucine, isoleucine, and methionine. In certain non-limiting embodiments $X_1$ is selected from the group consisting of alanine, valine, and leucine. In certain non-limiting embodiments $X_1$ is alanine. In further non-limiting embodiments, in addition to variable amino acid $X_1$, the amino acid sequence, SEQ ID NO:1, may further contain one additional variation which may be a substitution, an insertion, or a deletion of one natural or unnatural amino acid. In the embodiments described in this paragraph, in a subset of non-limiting embodiments, the ability of said Nox1 inhibitor has an $IC_{50}$ for inhibition of Nox1 which is at least 10-fold or at least 100-fold lower than its $IC_{50}$ against Nox2 or Nox 4. In non-limiting embodiments, the Nox1 inhibitor as described in this paragraph may comprise one or more or all L amino acids. In non-limiting embodiments, the Nox1 inhibitor as described in this paragraph may comprise one or more or all D amino acids. In one specific non-limiting embodiment, the Nox1 inhibitor is [$NH_3^+$]-EPVDALGKAKV-[$CONH2$] (SEQ ID NO:7).

In particular non-limiting embodiments of the invention the inhibitor of Nox1 comprises the amino acid sequence [$NH_3^+$]-PVDX$_1$LGKAKV-[$CONH2$] (SEQ ID NO:2) where $X_1$ is a natural or non-natural amino acid other than phenylalanine (F). In certain non-limiting embodiments $X_1$ is selected from the group consisting of alanine, valine, leucine, isoleucine, methionine, tyrosine, tryptophan, serine, threonine, asparagine, glutamine, aspartic acid, glutamic acid, cysteine, glycine, proline, arginine, histidine, and lysine. In certain non-limiting embodiments $X_1$ is selected from the group consisting of alanine, valine, leucine, isoleucine, methionine, tyrosine, and tryptophan. In certain non-limiting embodiments $X_1$ is selected from the group consisting of alanine, valine, leucine, isoleucine, and methionine. In certain non-limiting embodiments $X_1$ is selected from the group consisting of alanine, valine, and leucine. In certain non-limiting embodiments $X_1$ is alanine. In further non-limiting embodiments, in addition to variable amino acid $X_1$, the amino acid sequence, SEQ ID NO:2, may further contain one additional variation which may be a substitution, an insertion, or a deletion of one natural or unnatural amino acid. In the embodiments described in this paragraph, in a subset of non-limiting embodiments, the ability of said Nox1 inhibitor has an $IC_{50}$ for inhibition of Nox1 which is at least 10-fold or at least 100-fold lower than its $IC_{50}$ against Nox 2 or Nox 4. In non-limiting embodiments, the Nox1 inhibitor as described in this paragraph may comprise one or more or all L amino acids. In non-limiting embodiments, the Nox1 inhibitor as described in this paragraph may comprise one or more or all D amino acids.

In particular non-limiting embodiments of the invention the inhibitor of Nox1 comprises the amino acid sequence [$NH_3^+$]-EPVDX$_1$LGKAK-[$CONH2$] (SEQ ID NO:3) where $X_1$ is a natural or non-natural amino acid other than phenylalanine (F). In certain non-limiting embodiments $X_1$ is selected from the group consisting of alanine, valine, leucine, isoleucine, methionine, tyrosine, tryptophan, serine, threonine, asparagine, glutamine, aspartic acid, glutamic acid, cysteine, glycine, proline, arginine, histidine, and lysine. In certain non-limiting embodiments $X_1$ is selected from the group consisting of alanine, valine, leucine, isoleucine, methionine, tyrosine, and tryptophan. In certain non-limiting embodiments $X_1$ is selected from the group consisting of alanine, valine, leucine, isoleucine, and methionine. In certain non-limiting embodiments $X_1$ is selected from the group consisting of alanine, valine, and leucine. In certain non-limiting embodiments $X_1$ is alanine. In further non-limiting embodiments, in addition to variable amino acid $X_1$, the amino acid sequence, SEQ ID NO:3, may further contain one additional variation which may be a substitution, an insertion, or a deletion of one natural or unnatural amino acid. In the embodiments described in this paragraph, in a subset of non-limiting embodiments, the ability of said Nox1 inhibitor has an $IC_{50}$ for inhibition of Nox1 which is at least 10-fold or at least 100-fold lower than its $IC_{50}$ against Nox 2 or Nox 4. In non-limiting embodiments, the Nox1 inhibitor as described in this paragraph may comprise one or more or all L amino acids. In non-limiting embodiments, the Nox1 inhibitor as described in this paragraph may comprise one or more or all D amino acids.

In particular non-limiting embodiments of the invention the inhibitor of Nox1 comprises the amino acid sequence [$NH_3^+$]-VDX$_1$LGKAKV-[$CONH2$] (SEQ ID NO:4) where $X_1$ is a natural or non-natural amino acid other than phenylalanine (F). In certain non-limiting embodiments $X_1$ is selected from the group consisting of alanine, valine, leucine, isoleucine, methionine, tyrosine, tryptophan, serine, threonine, asparagine, glutamine, aspartic acid, glutamic acid, cysteine, glycine, proline, arginine, histidine, and lysine. In certain non-limiting embodiments $X_1$ is selected from the group consisting of alanine, valine, leucine, isoleucine, methionine, tyrosine, and tryptophan. In certain non-limiting embodiments $X_1$ is selected from the group consisting of alanine, valine, leucine, isoleucine, and methionine. In certain non-limiting embodiments $X_1$ is selected from the group consisting of alanine, valine, and leucine. In certain non-limiting embodiments $X_1$ is alanine. In further non-limiting embodiments, in addition to variable amino acid $X_1$, the amino acid sequence, SEQ ID NO:4, may further contain one additional variation which may be a substitution, an insertion, or a deletion of one natural or unnatural amino acid. In the embodiments described in this paragraph, in a subset of non-limiting embodiments, the ability of said Nox1 inhibitor has an $IC_{50}$ for inhibition of Nox1 which is at least 10-fold or at least 100-fold lower than its $IC_{50}$ against Nox 2 or Nox 4. In non-limiting embodiments, the Nox1 inhibitor as described in this paragraph may comprise one or more or all L amino acids. In non-limiting embodiments, the Nox1 inhibitor as described in this paragraph may comprise one or more or all D amino acids.

In particular non-limiting embodiments of the invention the inhibitor of Nox1 comprises the amino acid sequence [$NH_3^+$]-DX$_1$LGKAKV-[$CONH2$] (SEQ ID NO:5) where $X_1$ is a natural or non-natural amino acid other than phenylalanine (F). In certain non-limiting embodiments $X_1$ is selected from the group consisting of alanine, valine, leucine, isoleucine, methionine, tyrosine, tryptophan, serine, threonine, asparagine, glutamine, aspartic acid, glutamic acid, cysteine, glycine, proline, arginine, histidine, and lysine. In certain non-limiting embodiments $X_1$ is selected from the group consisting of alanine, valine, leucine, isoleucine, methionine, tyrosine, and tryptophan. In certain non-limiting embodiments $X_1$ is selected from the group consisting of alanine, valine, leucine, isoleucine, and methionine. In certain non-limiting embodiments $X_1$ is selected from the group consisting of alanine, valine, and leucine. In certain non-limiting embodiments $X_1$ is alanine. In further non-limiting embodiments, in addition to variable amino acid $X_1$, the amino acid sequence, SEQ ID NO:5, may further contain one additional variation which may be a substitution, an insertion, or a deletion of one natural or unnatural amino acid. In the embodiments described in this paragraph, in a subset of non-limiting embodiments, the ability of said Nox1 inhibitor has an $IC_{50}$ for inhibition of Nox1 which is at least 10-fold or at least 100-fold lower than its $IC_{50}$ against Nox 2 or Nox 4. In non-limiting embodiments, the Nox1 inhibitor as described in this paragraph may comprise one or more or all L amino acids. In non-limiting embodiments, the Nox1 inhibitor as described in this paragraph may comprise one or more or all D amino acids.

In particular non-limiting embodiments of the invention the inhibitor of Nox1 comprises the amino acid sequence $[NH_3^+]$-VDX$_1$LGKA-[CONH2](SEQ ID NO:6) where $X_1$ is a natural or non-natural amino acid other than phenylalanine (F). In certain non-limiting embodiments $X_1$ is selected from the group consisting of alanine, valine, leucine, isoleucine, methionine, tyrosine, tryptophan, serine, threonine, asparagine, glutamine, aspartic acid, glutamic acid, cysteine, glycine, proline, arginine, histidine, and lysine. In certain non-limiting embodiments $X_1$ is selected from the group consisting of alanine, valine, leucine, isoleucine, methionine, tyrosine, and tryptophan. In certain non-limiting embodiments $X_1$ is selected from the group consisting of alanine, valine, leucine, isoleucine, and methionine. In certain non-limiting embodiments $X_1$ is selected from the group consisting of alanine, valine, and leucine. In certain non-limiting embodiments $X_1$ is alanine. In further non-limiting embodiments, in addition to variable amino acid $X_1$, the amino acid sequence, SEQ ID NO:6, may further contain one additional variation which may be a substitution, an insertion, or a deletion of one natural or unnatural amino acid. In the embodiments described in this paragraph, in a subset of non-limiting embodiments, the ability of said Nox1 inhibitor has an $IC_{50}$ for inhibition of Nox1 which is at least 10-fold or at least 100-fold lower than its $IC_{50}$ against Nox 2 or Nox 4. In non-limiting embodiments, the Nox1 inhibitor as described in this paragraph may comprise one or more or all L amino acids. In non-limiting embodiments, the Nox1 inhibitor as described in this paragraph may comprise one or more or all D amino acids.

In particular non-limiting embodiments of the invention the inhibitor of Nox1 comprises the amino acid sequence $[NH_3^+]$-EP $X_2X_3X_1$LGKAKV-[CONH2] (SEQ ID NO:8) where either (i) $X_1$ is a natural or non-natural amino acid other than phenylalanine (F) and $X_2$ is valine and $X_3$ is aspartic acid, or (ii) $X_2$ is a natural or non-natural amino acid other than valine (V) and $X_1$ is phenylalanine and $X_3$ is aspartic acid, or (iii) $X_3$ is a natural or non-natural amino acid other than aspartic acid (D) and $X_1$ is phenylalanine and $X_2$ is valine, or (iv) $X_2X_3X_1$ is not VFD. In certain non-limiting embodiments $X_1$ is selected from the group consisting of alanine, valine, leucine, isoleucine, methionine, tyrosine, tryptophan, serine, threonine, asparagine, glutamine, aspartic acid, glutamic acid, cysteine, glycine, proline, arginine, histidine, and lysine. In certain non-limiting embodiments $X_2$ is selected from the group consisting of alanine, phenylalanine, leucine, isoleucine, methionine, tyrosine, tryptophan, serine, threonine, asparagine, glutamine, aspartic acid, glutamic acid, cysteine, glycine, proline, arginine, histidine, and lysine. In certain non-limiting embodiments $X_3$ is selected from the group consisting of alanine, valine, leucine, isoleucine, methionine, tyrosine, tryptophan, serine, threonine, phenylalanine, asparagine, glutamine, glutamic acid, cysteine, glycine, proline, arginine, histidine, and lysine. In certain non-limiting embodiments $X_1$ is selected from the group consisting of alanine, valine, leucine, isoleucine, methionine, tyrosine, and tryptophan. In certain non-limiting embodiments $X_2$ is selected from the group consisting of alanine, leucine, isoleucine, methionine, tyrosine, and tryptophan. In certain non-limiting embodiments $X_1$ is selected from the group consisting of alanine, valine, leucine, isoleucine, and methionine. In certain non-limiting embodiments $X_1$ is selected from the group consisting of alanine, valine, and leucine. In certain non-limiting embodiments $X_1$ is alanine. In further non-limiting embodiments, in addition to variable amino acid $X_1$, the amino acid sequence, SEQ ID NO:8, may further contain one additional variation which may be a substitution, an insertion, or a deletion of one natural or unnatural amino acid. In the embodiments described in this paragraph, in a subset of non-limiting embodiments, the ability of said Nox1 inhibitor has an $IC_{50}$ for inhibition of Nox1 which is at least 10-fold or at least 100-fold lower than its $IC_{50}$ against Nox 2 or Nox 4. In non-limiting embodiments, the Nox1 inhibitor as described in this paragraph may comprise one or more or all L amino acids. In non-limiting embodiments, the Nox1 inhibitor as described in this paragraph may comprise one or more or all D amino acids.

A peptide inhibitor comprising any of SEQ ID NO:1-8 as described above may be modified by conjugation to a molecule that enhances activity or stability, for example but not limited to a carbohydrate or a polyalkylene oxide such as but not limited to dextran or polyethylene glycol ("PEG", for example having a MW of between about 2 and 100 Kda or between about 10 and 60 kDa).

A peptide inhibitor having SEQ ID NO:1-8 as described above may optionally be comprised in a peptide having between about 6-100 residues or between about 7-100 residues or between about 8-100 residues or between about 9-100 residues or between about 10-100 residues or between about 11-100 residues or between about 6-50 residues or between about 7-50 residues or between about 8-50 residues or between about 9-50 residues or between about 10-50 residues or between about 11-50 residues or between about 6-30 residues or between about 7-30 residues or between about 8-30 residues or between about 9-30 residues or between about 10-30 residues or between about 11-30 residues or between about 6-20 residues or between about 7-20 residues or between about 8-20 residues or between about 9-20 residues or between about 10-20 residues or between about 11-20 residues or between about 6-15 residues or between about 7-15 residues or between about 8-15 residues or between about 9-15 residues or between about 10-15 residues or between about 11-15 residues. Said peptide may optionally be modified, for example by conjugation to a polyalkylene oxide, as set forth above.

A peptide inhibitor comprising any of SEQ ID NO:1-8 as described above may optionally be comprised in a fusion peptide where it is fused to a second biologically active molecule, for example an antibody or portion thereof, such as, but not limited to, an antibody or portion thereof directed to a colon carcinoma antigen or an antibody or portion thereof directed to an endothelial cell protein.

A Nox1 inhibitor, for example a peptide inhibitor comprising any of SEQ ID NO:1-8 as described herein (optionally modified as set forth above) may be used in a method of inhibiting the formation of a ROS by a cell comprising exposing the cell to an effective concentration of a Nox1 inhibitor that inhibits ROS formation by the cell.

A Nox1 inhibitor for example a peptide inhibitor comprising any of SEQ ID NO:1-8 as described herein (optionally modified as set forth above) may be used in a method of treating a subject having a disorder associated with ROS comprising administering, to the subject an effective amount of a Nox1 inhibitor that decreases ROS production in the subject. A subject, as referred to herein, may be a human or a non-human subject. Non-limiting examples of non-human subjects include a dog, a cat, a horse, a non-human primate, a bird, a mouse, a rat, a guinea pig, or a hamster.

A Nox1 inhibitor for example a peptide inhibitor comprising any of SEQ ID NO:1-8 as described herein (optionally modified as set forth above) may be used in a method of treating a subject having a disorder associated with Nox1 activity comprising administering, to the subject an effective amount of a Nox1 inhibitor that decreases ROS production in the subject. Non-limiting examples of disorders associated with Nox1 activity include hypertension, cancer, colon cancer, metastasis, atherosclerosis, aortic dissection, inflammation, *Helicobacter pylori*-associated gastric disease, Parkinson's Disease, and inflammatory bowel diseases such as Crohns disease and ulcerative colitis.

A Nox1 inhibitor for example a peptide inhibitor comprising any of SEQ ID NO:1-8 as described herein (optionally modified as set forth above) may be used in a method of treating a subject having a disorder associated with Nox1 activity comprising, administering, to the subject, a therapeutically effective amount of the Nox1 inhibitor. Non-limiting examples of disorders associated with Nox1 activity include hypertension, cancer, colon cancer, metastasis, atherosclerosis, aortic dissection, inflammation, *Helicobacter pylori*-associated gastric disease, Parkinson's Disease, and inflammatory bowel diseases such as Crohns disease and ulcerative colitis The present invention provides for a method of treating hypertension comprising administering, to a subject in need of such treatment, an effective amount of a Nox1 inhibitor, for example a peptide inhibitor comprising any of SEQ ID NO:1-8, as described herein (optionally modified as set forth above).

The present invention provides for a method of treating or reducing the risk of cancer in a subject comprising administering, to a subject in need of such treatment, an effective amount of a Nox1 inhibitor, for example a peptide inhibitor comprising any of SEQ ID NO:1-8, as described herein (optionally modified as set forth above). The cancer may be, for example and not by way of limitation, colon cancer, breast cancer, lung cancer, ovarian cancer, prostate cancer, melanoma, glioblastoma, renal carcinoma, pancreatic cancer, or bladder cancer.

The present invention provides for a method of treating or reducing the risk of metastasis of a cancer in a subject comprising administering, to a subject in need of such treatment, an effective amount of a Nox1 inhibitor, for example a peptide inhibitor comprising any of SEQ ID NO:1-8, as described herein (optionally modified as set forth above). The cancer may be, for example and not by way of limitation, colon cancer, breast cancer, lung cancer, ovarian cancer, prostate cancer, melanoma, glioblastoma, renal carcinoma, pancreatic cancer, or bladder cancer.

In non-limiting embodiments, an effective amount of a Nox1 inhibitor, for example but not limited to peptide inhibitors comprising any of SEQ ID NO:1-8 (optionally modified as set forth above), is an amount that specifically inhibits Nox1 generation of ROS and/or produces a local concentration, for example a blood concentration or a concentration in a tumor, of between about 0.5 and 100 nM or between about 0.5 and 50 nM or between about 0.5 and 20 nM in a subject. In certain non-limiting embodiments, an effective amount is an amount that reduces hypertension. In certain non-limiting embodiments, an effective amount is an amount that inhibits growth or spread of a cancer or reduces the risk of developing a cancer.

A Nox1 inhibitor according to the invention may be administered by any method known in the art including but not limited to intravenous, intraarterial, intraperitoneal, intrathecal, oral, subcutaneous, intramuscular, nasal, pulmonary, rectal or vaginal.

The present invention further provides for pharmaceutical compositions comprising a Nox1 inhibitor, for example but not limited to a peptide inhibitor comprising any of SEQ ID Nos:1-8 (optionally modified as set forth above), either in lyophilized form or in a suitable pharmaceutical carrier, for example but not limited to water or saline, optionally together with a physiologic buffer or other agents, such as osmotic agents, preservatives, etc.

Example

Experiments were performed to test the effect of NoxA1ds on $O_2^-$ production by Nox1. COS22 is a monkey kidney COST cell line expressing transgenic human p22phox and was produced by stable transfection of the full-length p22phox cDNA into parental COST wild-type cells [10]. COS22 cells were transfected with Nox1 to express the Nox1 enzyme and were then treated with either NoxA1ds or its scrambled control (SCRMB). Production of $O_2^-$ was calculated by monitoring the reduction of cytochrome c for 15 minutes post NADPH addition and subtracting baseline cytochrome c reduction occurring in the presence of SOD. As shown in FIG. 3A, increasing concentrations (from 0.1 nM to 10,000 nM) of NoxA1ds caused a dose dependent inhibition of $O_2^-$ production with an $IC_{50}$ of 19 nM. Maximal inhibition of 88% of total $O_2^-$ production was achieved at a dose of 1.0 µM NoxA1ds. Increasing concentrations of SCRMB, however, did not inhibit Nox1-derived $O_2^-$ production (FIG. 3B). Similar results were obtained when, after 10 min incubation with NoxA1ds [dark gray bar] or SCRMB [medium gray bar], production of superoxide by HEK Nox1 cells was measured via reduction of cytochrome c (FIG. 5).

To test whether the inhibitory effect of NoxA1ds is specific to Nox1, the effect of NoxA1ds was tested on cells expressing Nox2, Nox4, and Nox5 as well as on purified xanthine oxidase enzyme. To test the effect on Nox2, production of $O_2^-$ was measured by the reduction of cytochrome c by cell lysates from COS cells transiently transfected with the Nox2 oxidase, stimulated with LiDS, and the treated with increasing concentrations of NoxA1ds (from 0.1 nM to 10,000 nM). Similarly, production of $H_2O_2$ was measured by Amplex red fluorescence by COS cells transiently transfected with the Nox4 oxidase and treated with increasing concentrations of NoxA1ds (from 100 nM to 10,000 nM). Production of $O_2^-$ was also measured by the reduction of cytochrome c by cell lysates from HEK293 cells stably transfected with the Nox5 oxidase stimulated with $Ca^{2+}$, and treated with increasing concentrations of NoxA1ds (from 0.1 nM to 10,000 nM). Finally, production of $O_2^-$ was measured by Electron Paramagnetic Resonance from pure xanthine oxidase enzyme preparations, stimulated with hypoxanthine and treated with increasing concentrations of NoxA1ds (from 0.1 nM to 10,000 nM). The results of these studies are shown in FIG. 4A-D, respectively. In all instances NoxA1ds did not exhibit a significant inhibitory effect.

Example: NoxA1ds Binds to Nox1 and Disrupts Interaction with NoxA1

An ELISA of Nox1:NoxA1ds interaction was performed as follows. Neutravidin coated plates were incubated with biotin-tagged NoxA1ds (Biotin-NoxA1ds) or biotin-tagged SCRMB (Biotin-SCRMB) before addition of cell membranes prepared from cells transfected with Nox1 (Nox1 membrane) or transfected with an empty vector (COS22 membrane). Bound Nox1 was detected through a FITC conjugated secondary antibody (αRabbit Ab Sigma F9887) bound to the Nox1 primary antibody (rabbit αNox1 Ab (SC-25545, Santa Cruz Biotechnology)). FITC fluorescence was expressed as binding as % COS22 membranes on each experimental day. As shown in FIG. 6A, there was no difference in binding between COS22 membranes and Nox1 membranes incubated with Biotin-SCRMB whereas membranes incubated with Biotin-NoxA1ds showed a significant increase in binding when transfected with Nox1. To further confirm the association, image cross correlation spectroscopy (ICCS) was used to determine patterns in signal fluctuation between rhodamine-labeled NoxA1ds (R-NoxA1ds) and Nox1-YFP though a sequence of 100 images 0.05 s apart. Correlation and cross-correlation was calculated using an ImageJ plugin. As shown in FIG. 6B, fractional binding of Nox1-YFP and R-NoxA1ds approaches a value of 1.0, indicative of a strong interaction between the two molecules. Competition between R-NoxA1ds and unlabelled NoxA1ds significantly reduced the fractional binding.

Figure 7A:
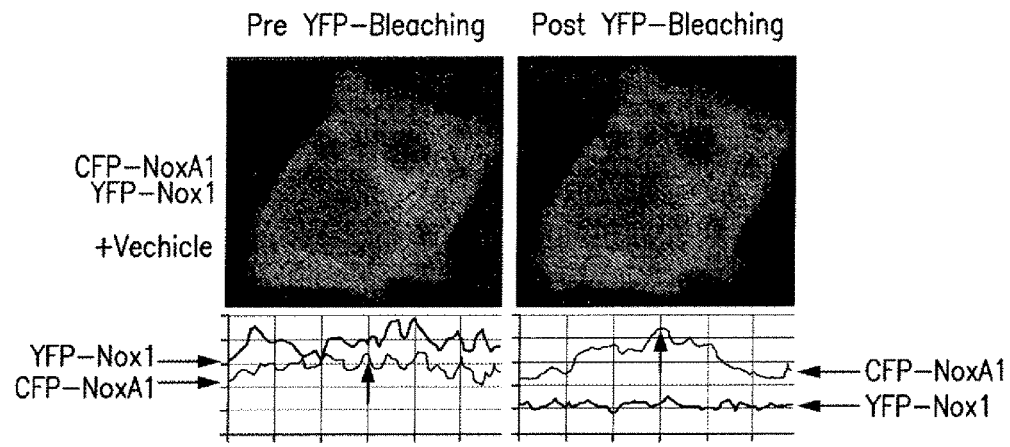
FIG. 7A-D. Analysis of FRET between Nox1-YFP and NoxA1-CFP transfected COS22 cells in the presence or absence of 10 µM NoxA1ds or SCRMB. (A) CFP-NoxA1 and YFP-Nox1 vehicle control. (B) CFP-NoxA1 and YFP-Nox-1 with SCRMB peptide. (C) CFP-NoxA1 and YFP-Nox1 with NoxA1ds added. (D) Percent FRET efficiency showing that NoxA1ds decreases FRET between Nox1 and NoxA1. Images are representative of three experiments where four cells were imaged in each experiment. *** $p<0.001$, one-way ANOVA with Bonferroni post-test.
Figure 7B:
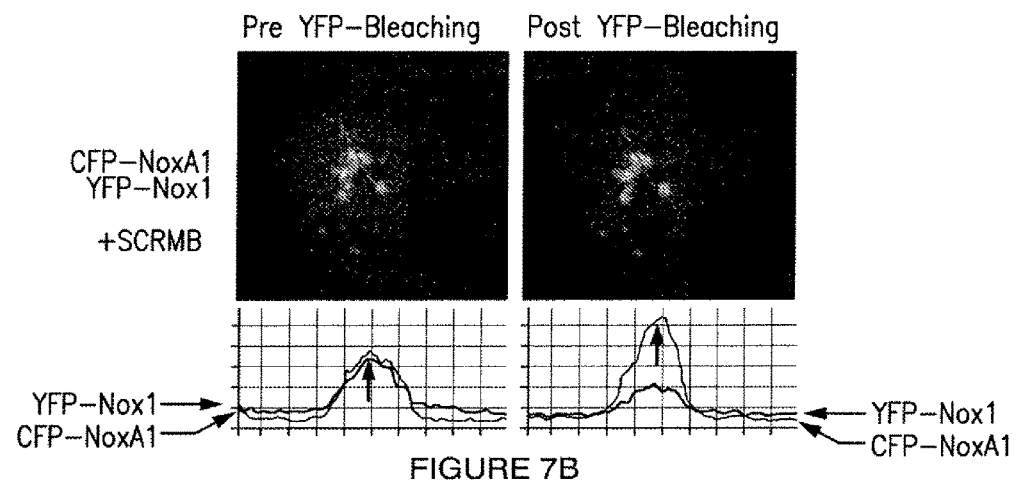
Figure 7C:
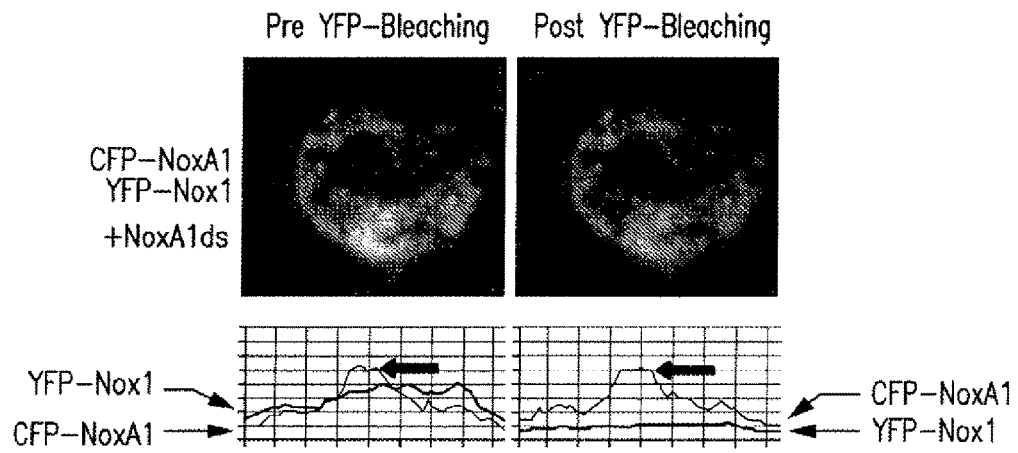
Figure 7D:
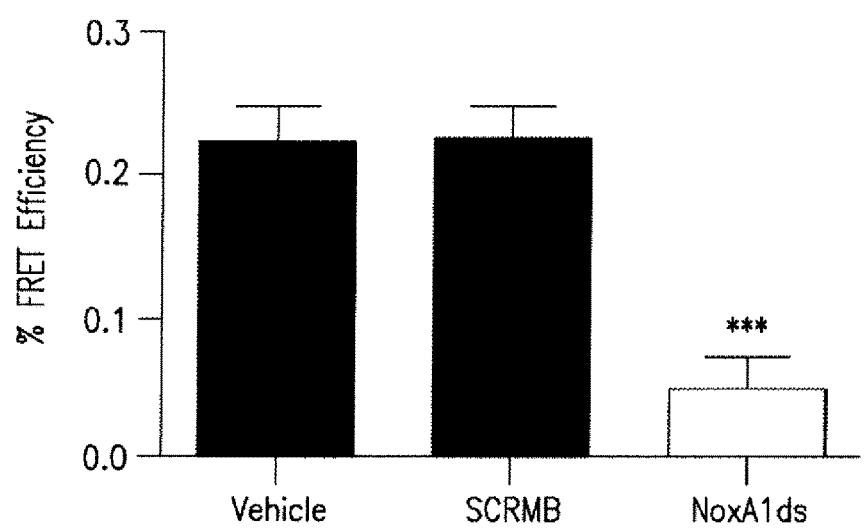

FRET (fluorescence resonance energy transfer) studies were performed to study the effect of NoxA1ds on the interaction between Nox1 and NoxA1: In particular, FRET between Nox1-YFP and NoxA1-CFP transfected COS22 cells in the presence or absence of 10 μM NoxA1ds or SCRMB was evaluated. Relative fluorescence of CFP is green while YFP is red. Traces underneath the images indicate fluorescent intensities of CFP and YFP underneath the arrow overlaid on each cell. When transfected COS22 cells were treated with vehicle (phosphate buffered saline) for one hour prior to imaging cells, photobleaching of Nox1-YFP was complete and resulted in a concomitant increase in CFP fluorescence (FIG. 7A). Similarly, when transfected COS22 cells were treated with 10 μM SCRMB peptide for one hour prior to imaging cells, photobleaching of Nox1-YFP was complete and also resulted in a concomitant increase in CFP fluorescence (FIG. 7B). However, when transfected COS22 cells were treated with 10 μM NoxA1ds peptide for one hour prior to imaging cells, photobleaching of Nox1-YFP was complete but did not result in a concomitant increase in CFP fluorescence (FIG. 7C). FIG. 7D shows a quantification of FRET efficiency from images A-C. These results support disruption of interaction between Nox1 and NoxA1 by NoxA1ds.

Example: Effect of NoxA1ds During Cell Stress

Figure 8:
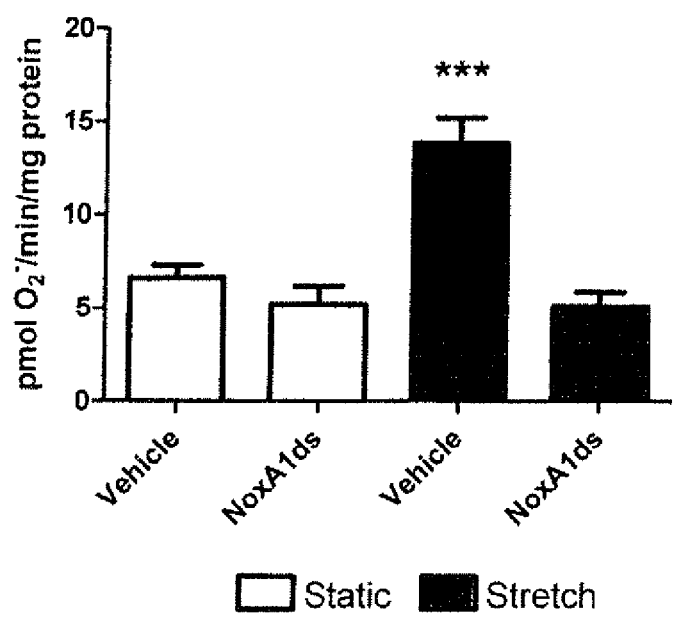
FIG. 8. NoxA1ds attenuates stretch-induced $O_2^-$ production: Effect of NoxA1ds on $O_2^-$ production by rat aortic smooth muscle cells subjected to static conditions or cyclic stretch (10%, 1 Hz, 24 hrs). NoxA1ds was added 4 hrs before measuring $O_2^-$ production. Under static conditions, 10 µM NoxA1ds had a negligible effect on $O_2^-$ production. Cell stretch caused a 2 fold increase in $O_2^-$ production that was completely abrogated by treatment with NoxA1ds. n=3, *$p<0.05$ one-way ANOVA with Bonferroni post-test versus static+vehicle treatment.

Cyclic stretching of vascular cells occurs as a result of the pulsatile nature of blood flow but is increased in hypertensive states, and has been associated with generation of ROS and possibly cell proliferation [11, 12]. To test whether inhibition of Nox1 affects ROS produced as a result of blood vessel stress or expansion, RASMC were treated with cyclic stretch (10%, 1 Hz) for 24 hrs, and then, at t=20 hrs, 5.0 μM NoxA1ds was added to the media. At the end of 24 hrs, cells were lysed and membrane fraction $O_2^-$ production was measured using cytochrome c. As shown in FIG. 8, NoxA1ds inhibited cyclic stretch-induced $O_2^-$ production in rat aortic smooth muscle cells.

Figure 9A:
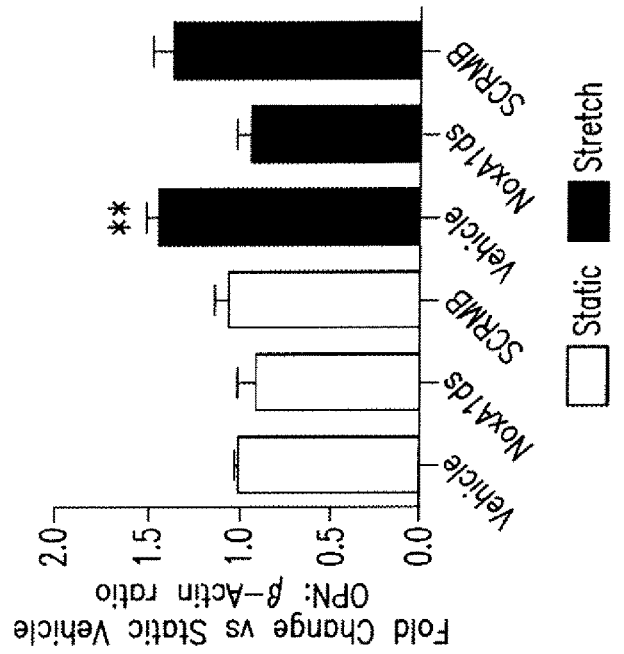
FIG. 9A-D. (A) Fold-change of calponin, a marker of the synthetic smooth muscle phenotype, in rat aortic smooth muscle cells subjected to static or stretch conditions and treated with vehicle, NoxA1ds or SCRMB peptides. (B) Western blot showing calponin versus β-actin expression in cells during static or stretch periods, with bar showing lanes reflecting addition of NoxA1ds. The lanes reflect the treatments shown above them. (C) Fold-change of osteopontin ("OPN"), a marker of the contractile phenotype, in rat aortic smooth muscle cells subjected to static or stretch conditions and treated with vehicle, NoxA1ds or SCRMB peptides. (D) Western blot showing OPN versus β-actin expression in cells during static or stretch periods, with bar showing lanes reflecting addition of NoxA1ds. The lanes reflect the treatments shown above them. n=3, *$p<0.05$ one-way ANOVA with Bonferroni post-test versus static+vehicle treatment. $p<0.05$ vs. static vehicle.
Figure 9B:
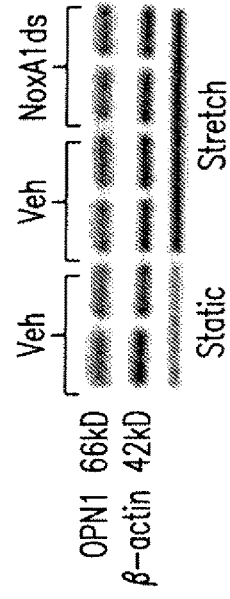
Figure 9C:
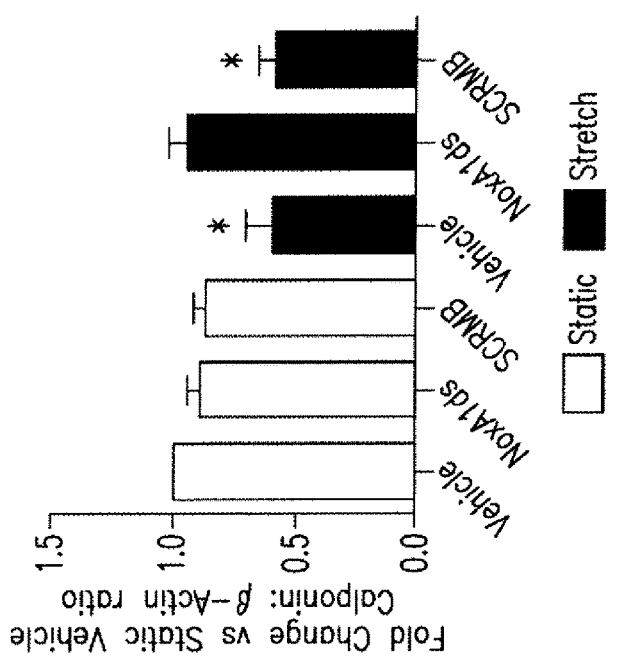
Figure 9D:
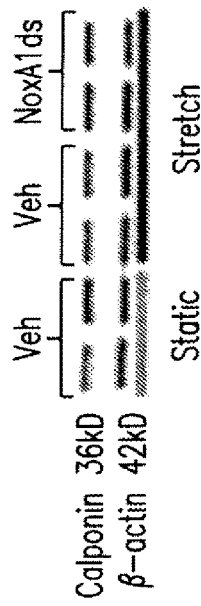

NoxA1ds was observed to reverse stretch induced phenotypic changes, as follows. The effect of Nox1 inhibition on the expression of certain protein markers of rat aortic smooth muscle cell contractile vs. synthetic phenotypes was evaluated. Cells were subjected to 24 hrs of cyclic stretch (10%, 1 Hz) with 10 μM NoxA1ds or SCRMB control being added every four hours. As shown in FIG. 9A, calponin (a marker of the synthetic phenotype) expression decreased after stretch. Calponin expression during stretch was rescued by the addition of 10 μM NoxA1ds, yet was unaffected by the addition of 10 μM scrambled peptide (SCRMB). A representative Western blot is shown below the graph (FIG. 9B). Osteopontin (OPN, a marker of the contractile phenotype), expression increased after 24 hrs of stretch. OPN1 expression during stretch returned to levels observed in the absence of stretch after the addition of 10 μM NoxA1ds, yet was unaffected by the addition of 10 μM SCRMB (FIG. 9C, representative blot FIG. 9D).

Figure 10:
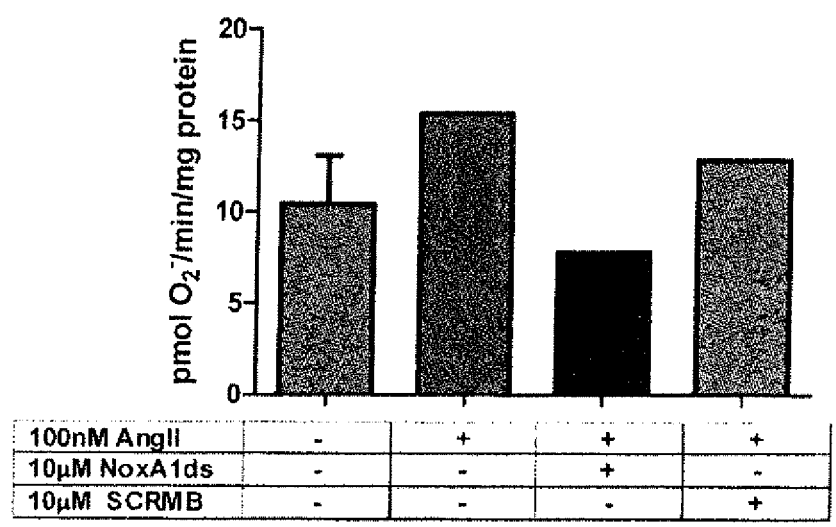
FIG. 10. $O_2^-$ Production by human pulmonary artery endothelial cells ("HPAEC") which were either (i) untreated; (ii) treated with 100 nM angiotensin II; (iii) treated with 100 nM angiotensin II and 10 µM NoxA1ds; or (iv) treated with 100 nM angiotensin II and 10 µM SCRMB peptide. Results represent mean±SEM, n=5-9, 2-3 separate experiments.

In further studies, HPAEC constitutively expressing Nox1 were treated with vehicle or Angiotensin II (AngII, one mediator of hypertension) alone or in combination with NoxA1ds, or SCRMB for 1 hr. $O_2^-$ production was then measured via reduction of cytochrome c. As shown in FIG. 10, the results indicate that AngII induces $O_2^-$ production in human pulmonary endothelial cells that was completely inhibited by NoxA1ds.

Figure 11:
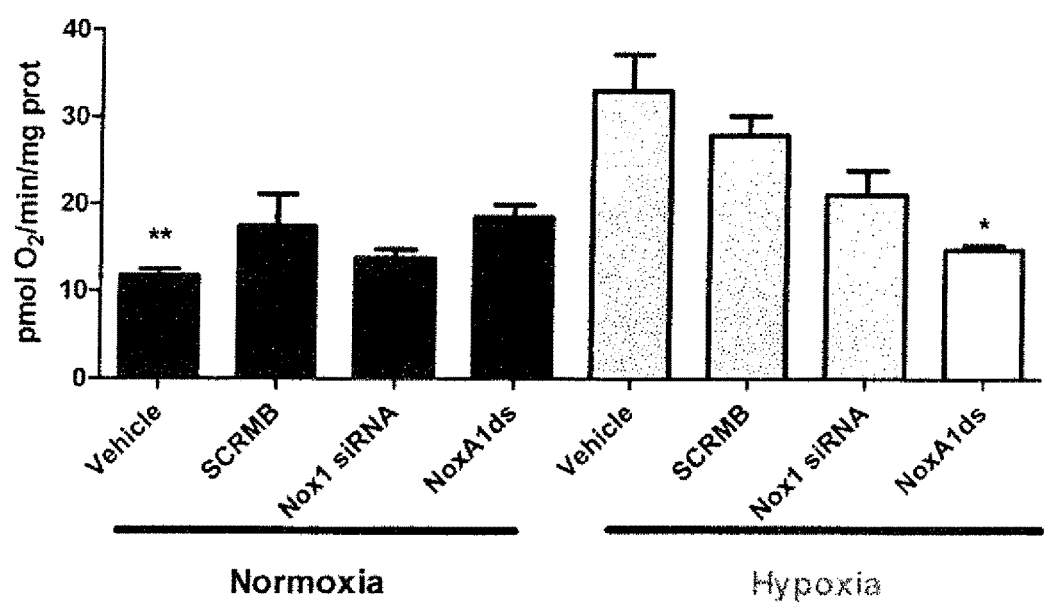
FIG. 11. NoxA1ds attenuates hypoxia induced $O_2^-$ production by HPACs. n=9, three separate experiments. * $p<0.05$, ** $p<0.01$, vs. hypoxic, vehicle-treated cells, one-way ANOVA with Bonferroni post-test.

Experiments were also performed to evaluate the effect of NoxA1ds on hypoxia-induced superoxide production by human pulmonary artery endothelial cells. SCRMB, NoxA1ds, and Nox1 siRNA had a negligible effect on $O_2^-$ production under nogmoxic conditions. Hypoxia (1.0% O2, 24 hrs) treatment resulted in a three-fold increase in $O_2^-$ production that was unaffected by SCRMB. Upon treatment with NoxA1ds, $O_2^-$ production by cells subjected to hypoxia returned to the amount observed under normoxia (FIG. 11).

Example: NoxA1ds Reduces Cell Migration

Figure 12A:
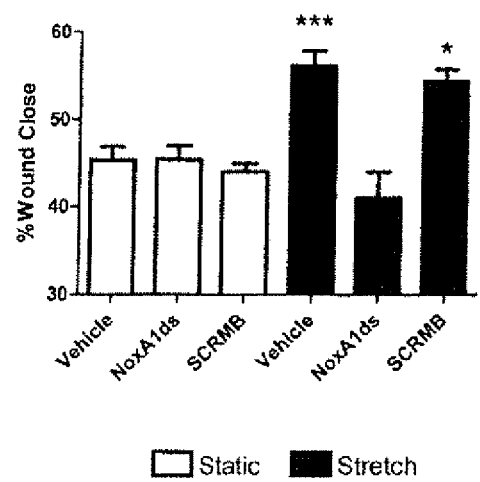
FIG. 12A-B. Effect of NoxA1ds on cell migration of stretched and non-stretched cells. (A). Bar graph showing effect of NoxA1ds versus vehicle and SCRMB control on migration by static and stretched cells, where migration is reflected by percent wound closure. (B) Micrograph showing effect of NoxA1ds versus vehicle on stretched cells at 0 and 24 hour time points, with static cells treated by vehicle depicted for comparison. *$p<0.05$, ***$p<0.001$ versus static+vehicle treatment, one-way ANOVA with Bonferroni post-test.
Figure 12B:
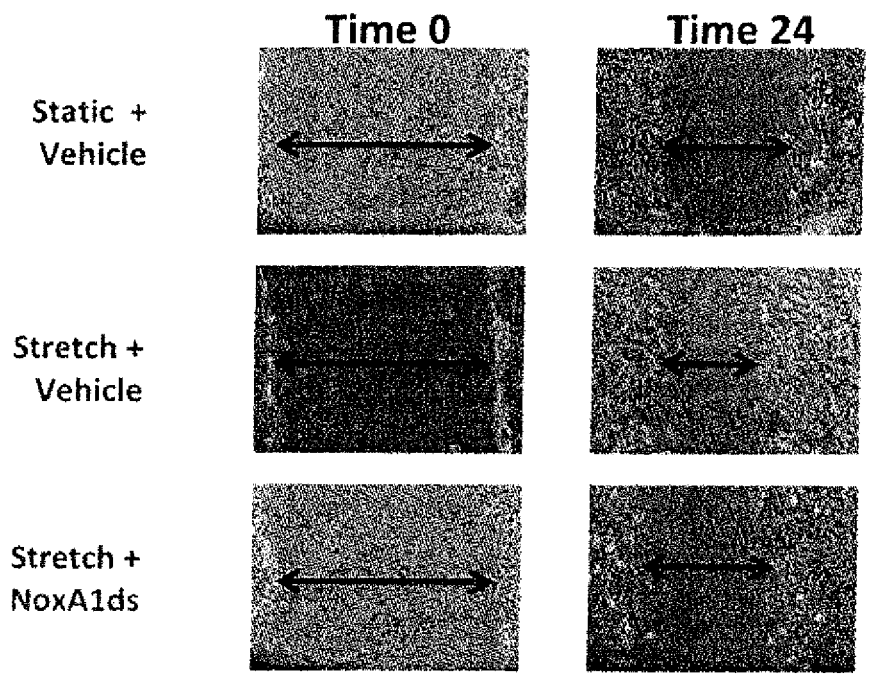

The effect on NoxA1ds on stretch-induced migration of rat aortic smooth muscle cells was studied. Cell monolayer cultures with an introduced gap ("wound") were subjected to 24 hrs of cyclic stretch (10%, 1 Hz) with 10 μM NoxA1ds or SCRMB control being added every four hours. Cell migration may be assessed as the distance the wound has closed, where greater culture corresponds to greater migration. Cell migration increased as a result of cyclic stretch. As shown in FIGS. 12A-B, treatment with NoxA1ds reduced migration to levels observed in non-stretched cells.

Example: NoxA1ds Enters Cancer Cells and Inhibits Ros Production

Figure 13A:
FIG. 13A-E. (A) Differential interference contrast ("DIC") micrograph showing colon adenocarcinoma cells incubated with fluorescein isothiocyanate ("FITC")-NoxA1ds. (B). Fluorescence microscopy showing FITC-NoxA1ds distribution in cells. (C) Fluorescence microscopy showing FITC-NoxA1ds localization in cells stained with DAPI (4',6-diamidino-2-phenylindole, which is blue fluorescent and binds strongly to A-T rich regions in DNA). (D) DIC micrograph of cells treated with FITC-NoxA1ds and stained with DAPI. (E) Production of $O_2^-$ by HT-29 cells treated with increasing concentration of NoxA1ds. Values are expressed as n=9, three separate experiments. *** $p<0.05$ for 0.5, 1, and 5 µM NoxA1ds vs 0 µM NoxA1ds by one-way ANOVA with Bonferroni post-test.
Figure 13B:
Figure 13C:
Figure 13D:
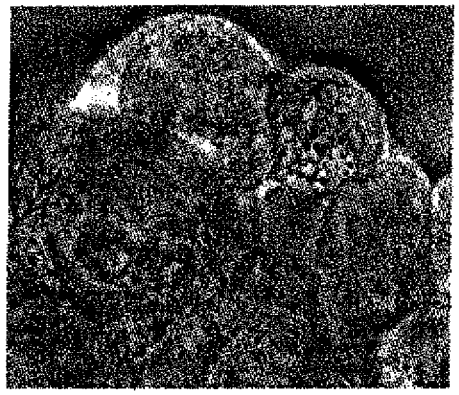
Figure 13E:
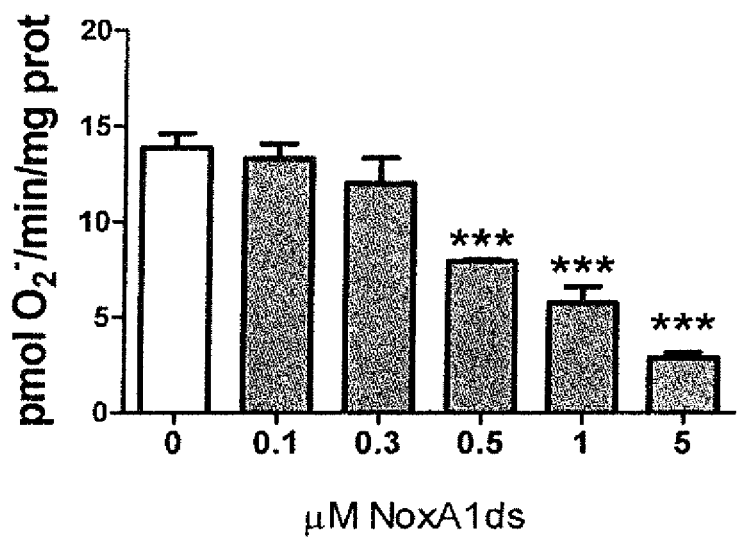

FITC-labeled NoxA1ds and native NoxA1ds were incubated with HT-29 colon adenocarcinoma cells. HT-29 cells bear the distinction of having abundant Nox1 expression while not expressing Nox2, Nox4, or Nox5. FITC-labeled NoxA1ds was incubated with the cells for 1 hr prior to imaging. Confocal microscopy of these cells (FIG. 13A-D) indicates that FITC-NoxA1ds penetrated the extracellular membrane and that its distribution is cytosolic and perinuclear. As measured by SOD inhibitable reduction of cytochrome c, increasing doses of NoxA1ds caused dose-dependent inhibition of $O_2^-$ production by HT-29 cells (FIG. 13E). SCRMB peptide did not inhibit $O_2^-$ production.

REFERENCES

1. White, C. R., et al., Superoxide and peroxynitrite in atherosclerosis. Proc Natl Acad Sci USA, 1994. 91(3): p. 1044-8.

2. Al Ghouleh, I., et al., Oxidases and peroxidases in cardiovascular and lung disease: New concepts in reactive oxygen species signaling. Free Radic Biol Med, 2011. 51(7): p. 1271-88.
3. Nisimoto, Y., et al., The p67(phox) activation domain regulates electron flow from NADPH to flavin in flavocytochrome b(558). J Biol Chem, 1999. 274(33): p. 22999-3005.
4. Han, C. H., et al., Regulation of the neutrophil respiratory burst oxidase. Identification of an activation domain in p67(phox). J Biol Chem, 1998. 273(27): p. 16663-8.
5. Maehara, Y., et al., A conserved region between the TPR and activation domains of p67phox participates in activation of the phagocyte NADPH oxidase. J Biol Chem, 2010. 285(41): p. 31435-45.
6. Gianni, D., et al., A novel and specific NADPH oxidase-1 (Nox1) small-molecule inhibitor blocks the formation of functional invadopodia in human colon cancer cells. ACS Chem Biol, 2010. 5(10): p. 981-93.
7. Dikalova, A., et al., Nox1 overexpression potentiates angiotensin II-induced hypertension and vascular smooth muscle hypertrophy in transgenic mice. Circulation, 2005. 112(17): p. 2668-76.
8. Rey, F. E., et al., Novel competitive inhibitor of NAD(P)H oxidase assembly attenuates vascular O(2)(−) and systolic blood pressure in mice. Circ Res, 2001. 89(5): p. 408-14.
9. Kim, J. A., et al., NADPH oxidase inhibitors: a patent review. Expert Opin Ther Pat, 2011. 21(8): p. 1147-58.
10. Yu L. et al., J. Biol. Chem, 1997. 272: p. 27288-27294.
11. Howard et al., Am. J. Physiol. Cell Physiol., 1997. 272(2): p. C421-C427.
12. Standley et al., Am. J. Physiol. Heart, 2002. 283(5): p. H19-7-H1914)

Various patent and non-patent publications are cited herein, the contents of which are hereby incorporated by reference in their entireties.

What is claimed is:

1. A method of treating a subject having colon cancer comprising administering, to the subject, an effective amount of a NADPH oxidase-1 (Nox1) inhibitor comprising the amino acid sequence $[NH_3^+]$-EPVDX$_1$LGKAKV-$[CONH_2]$ (SEQ ID NO:1), wherein $X_1$ is a natural or non-natural amino acid other than phenylalanine, and further comprises up to one additional amino acid variation selected from the group consisting of a substitution, an insertion, and a deletion of one natural or unnatural amino acid.

2. The method of claim 1, wherein the Nox1 inhibitor decreases reactive oxygen species production in the subject having colon cancer.

3. The method of claim 1, wherein the Nox1 inhibitor reduces cancer cell metastasis in the subject having colon cancer.

* * * * *